(12) United States Patent
Hatano et al.

(10) Patent No.: US 10,379,069 B2
(45) Date of Patent: Aug. 13, 2019

(54) MAGNETISM MEASURING DEVICE

(71) Applicant: Renesas Electronics Corporation, Koutou-ku, Tokyo (JP)

(72) Inventors: Yuji Hatano, Koutou-ku (JP); Jun Ueno, Koutou-ku (JP); Takenori Okitaka, Koutou-ku (JP); Keiro Komatsu, Koutou-ku (JP)

(73) Assignee: Renesas Electronics Corporation, Koutou-ku, Tokyo (JP)

( * ) Notice: Subject to any disclaimer, the term of this patent is extended or adjusted under 35 U.S.C. 154(b) by 325 days.

(21) Appl. No.: 14/969,742

(22) Filed: Dec. 15, 2015

(65) Prior Publication Data

US 2016/0174867 A1 Jun. 23, 2016

(30) Foreign Application Priority Data

Dec. 17, 2014 (JP) ................. 2014-255560

(51) Int. Cl.
*A61B 5/00* (2006.01)
*G01N 24/10* (2006.01)
*G01R 33/24* (2006.01)
*G01R 33/60* (2006.01)
*A61B 5/05* (2006.01)

(52) U.S. Cl.
CPC ............. *G01N 24/10* (2013.01); *G01R 33/24* (2013.01); *G01R 33/60* (2013.01); *A61B 5/05* (2013.01)

(58) Field of Classification Search
CPC ........ G01N 24/10; G01R 33/24; G01R 33/60; A61B 5/05
See application file for complete search history.

(56) References Cited

U.S. PATENT DOCUMENTS

| 8,193,808 B2 * | 6/2012 | Fu ......................... G01N 24/088 |
| | | 324/304 |
| 2010/0216143 A1 | 8/2010 | King et al. |
| 2011/0062957 A1 * | 3/2011 | Fu ......................... G01N 24/088 |
| | | 324/307 |

(Continued)

FOREIGN PATENT DOCUMENTS

| JP | H11-173987 A | 7/1999 |
| JP | 2005-526253 A | 9/2005 |
| JP | 2012-95803 A | 5/2012 |

OTHER PUBLICATIONS

S. Steinert, et al., "High sensitivity magnetic imaging using an array of spins in diamond", Review of Scientific Instrument 81, 2010, pp. 1-13, 043705-1~5.

(Continued)

*Primary Examiner* — Joel Lamprecht
(74) *Attorney, Agent, or Firm* — Sughrue Mion, PLLC

(57) ABSTRACT

A magnetism measuring device includes a light source unit, a diamond crystal and an image sensor. The light source unit irradiates the diamond crystal with an excitation light, and irradiates the image sensor with a fluorescent light generated by the diamond crystal. The diamond crystal includes a plurality of nitrogen-vacancy pairs. The image sensor detects an intensity of the fluorescent light, which is generated from the diamond crystal, by a plurality of pixels. The image sensor and the light source unit are disposed so as to be contained within a projection area of the diamond crystal.

16 Claims, 14 Drawing Sheets

(56) References Cited

U.S. PATENT DOCUMENTS

| | | | | |
|---|---|---|---|---|
| 2014/0035584 A1* | 2/2014 | Twitchen | ......... | B01L 3/502707 |
| | | | | 324/321 |
| 2015/0253355 A1* | 9/2015 | Grinolds | ............. | G01R 33/022 |
| | | | | 850/40 |
| 2016/0161429 A1* | 6/2016 | Englund | .............. | G01N 24/006 |
| | | | | 324/304 |
| 2016/0216341 A1* | 7/2016 | Boesch | ............... | G01R 33/032 |

OTHER PUBLICATIONS

Communication dated Feb. 27, 2018 issued by the Japanese Patent Office in counterpart application No. 2014-255560.

\* cited by examiner

MAGNETISM MEASURING DEVICE

CROSS-REFERENCE TO RELATED APPLICATION

The present application claims priority from Japanese Patent Application No. 2014-255560 filed on Dec. 17, 2014, the content of which is hereby incorporated by reference into this application.

TECHNICAL FIELD OF THE INVENTION

The present invention relates to a magnetism measuring device, and particularly relates to a technology effectively applied to a magnetic field detection using nitrogen-vacancy pairs of a diamond crystal in the atmospheric air at a normal temperature.

BACKGROUND OF THE INVENTION

As a biomagnetism measuring system of medical equipment, for example, a magnetoencephalography system has been known. The magnetoencephalography system measures a weak magnetic field generated by brain neurons from the outside, and inspects an active portion in a brain and a degree of the activation thereof with high accuracy.

This type of biomagnetism measuring system includes a high-sensitivity magnetism measuring device. As the high-sensitivity magnetism measuring device capable of detecting a weak biovector magnetic field such as brain magnetism, a superconducting quantum interference device (SQUID) has been used, but a cryogenic environment is necessary for its operation.

On the other hand, as a high-sensitivity magnetic field measuring device which can operate in the atmospheric air at a normal temperature, a diamond crystal which includes nitrogen-vacancy pairs has been proposed (for example, see S. Steinert, F. Dolde, P. Neumann, A. Aird, B. Naydenov, G. Balasubramanian, F. Jelezko, and J. Wrachtrup; "High sensitivity magnetic imaging using an array of spins in diamond", Review of Scientific Instrument 81, 043705-1~5, (2010) (Non-Patent Document 1)).

In the Non-Patent Document 1, the following contents are disclosed. A green laser beam is used as a viridian light source which irradiates the diamond crystal serving as a sensor to measure the magnetic field with an excitation light, and a charge coupled device (CCD) image sensor is used to detect a red fluorescent output from the diamond crystal. The magnetic field is measured from a position of the microwave frequency at a minimum fluorescence intensity in a microwave frequency dependency of a red fluorescence intensity acquired by sweeping the frequency of the microwave emitted to the diamond crystal.

SUMMARY OF THE INVENTION

In FIG. 3 of the Non-Patent Document 1 described above, a light path in a magnetism measuring device is disclosed. The light path of the magnetism measuring device reaches the CCD image sensor from the green laser beam source through the diamond crystal.

In FIG. 3, the CCD image sensor is depicted in a larger scale than the diamond crystal. Although FIG. 3 is a schematic view and a lens system is not illustrated, the measurable range is estimated to be smaller than at least the size of the CCD image sensor based on the description that the gaps between main parts are 10 µm to 20 µm and 30 µm to 40 µm in the measurement result of FIG. 5.

Here, the case where a number of the magnetism measuring devices of the Non-Patent Document 1 described above are arranged in a planar shape to densely measure the magnetic field of a body surface is assumed. Such measurement is used in the case where the state of the inner body is estimated from the state of the body surface, and for example, magnetoencephalography to estimate a blood stream distribution in a brain from the magnetic field of the brain surface is one type thereof.

In a wearable diagnosis device in which the magnetism measuring devices are arranged on the body surface to make it possible to detect information of the inner body, a detectable depth depends on a sensitivity of the magnetism measuring device, and spatial resolution depends on the surface density of the magnetism measuring devices.

Therefore, it is desirable that the magnetism measuring devices are densely arranged on the body surface. As the surface density increases, high spatial resolution can be realized up to a deep position. Accordingly, in such a usage, it is desirable that the image sensors are densely arranged on the body surface without a gap.

However, in the case of the magnetism measuring device of the Non-Patent Document 1, since the CCD image sensor is estimated to be larger than the diamond crystal as described above, when the magnetism measuring devices are arranged on the body surface, the arrangement is constrained by the size of the CCD image sensor.

Therefore, it is difficult to densely arrange the diamond crystals on the body surface, so that the detectable spatial resolution is lowered and the performance of the wearable diagnosis device is degraded.

A magnetism measuring device according to an embodiment includes: a diamond crystal; an image sensor and a light source unit. The diamond crystal has a plurality of nitrogen-vacancy pairs. The image sensor detects an intensity of a fluorescent light emitted from the diamond crystal by a plurality of pixels. The light source unit irradiates the diamond crystal with an excitation light and irradiates the image sensor with the fluorescent light emitted from the diamond crystal. Then, the image sensor and the light source unit are disposed so as to be contained within a projection area of the diamond crystal.

According to the embodiment described above, it is possible to improve the spatial resolution in magnetism measurement.

BRIEF DESCRIPTIONS OF THE DRAWINGS

DESCRIPTIONS OF THE PREFERRED EMBODIMENTS

Figure 1:
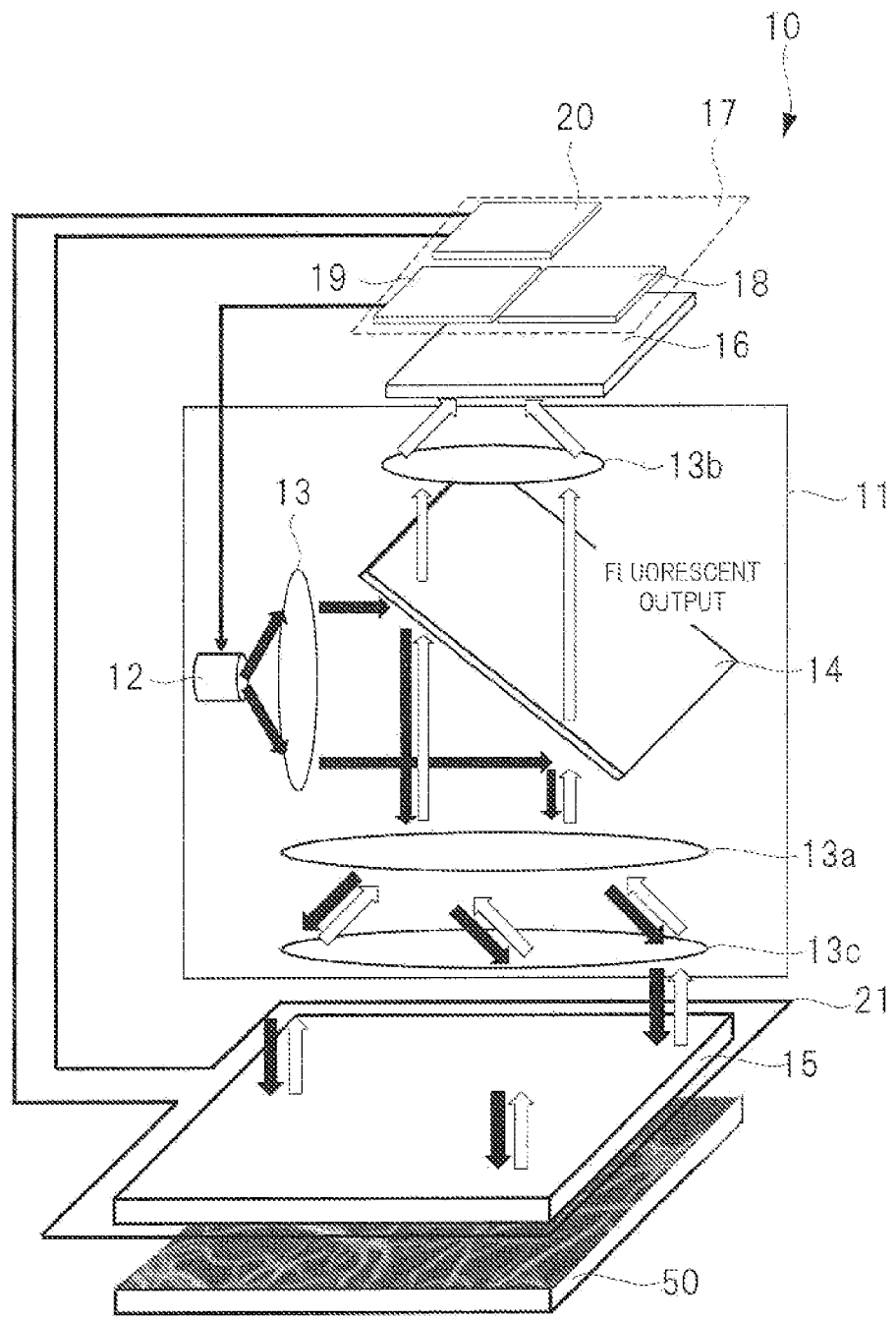
FIG. 1 is an explanatory diagram illustrating an example of a configuration of a magnetism measuring device according to the first embodiment.

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like) , the number of the elements is not limited to a specific number unless otherwise stated or except the case where the number is apparently limited to a specific number in principle, and the number larger or smaller than the specified number is also applicable.

Further, in the embodiments described below, it goes without saying that the components (including element steps) are not always indispensable unless otherwise stated or except the case where the components are apparently indispensable in principle.

Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Also, the same components are denoted by the same reference characters throughout the drawings for describing the embodiments, and the repetitive description thereof is omitted. Note that hatching is sometimes used even in a plan view so as to make the drawings easy to see.

Hereinafter, embodiments will be described in detail.

(First Embodiment)

<Outline>

In the outline of this embodiment, a lens system, in particular, a lens 13c in a magnetism measuring device 10 is configured to set a ratio between an area of an image sensor 16 and an area of a diamond crystal 15 to be 1:n. With this configuration, a viridian light source 12, lenses 13 and 13a to 13c, a dichroic mirror 14, the image sensor 16 and a control unit 17 positioned above the diamond crystal 15 can be made smaller than a projection area of the diamond crystal 15. As a result, the magnetism measuring devices 10 can be densely arranged, so that a biomagnetism can be detected with high accuracy.

(Configuration Example of Magnetism Measuring Device)

FIG. 1 is an explanatory diagram illustrating an example of a configuration of the magnetism measuring device 10 according to the first embodiment.

The magnetism measuring device 10 is a biomagnetism detection device which is used in medical equipment such as a biomagnetism measuring device including magnetoencephalography, magnetocardiography or magnetomyography. For example, the magnetoencephalography measures and analyzes a weak magnetic field generated by a nervous activity of the brain in a noninvasive manner through a scalp.

As illustrated in FIG. 1, the magnetism measuring device 10 includes a light source unit 11, the diamond crystal 15, the image sensor 16, the control unit 17 and a coil 21.

The light source unit 11 is made up of the viridian light source 12, the lenses 13, 13a, 13b and 13c and the dichroic mirror 14. The viridian light source 12 serving as a light source outputs an excitation light of a wavelength of, for example, about 533 nm or shorter.

The lens 13 serving as a first lens collects the excitation light output from the viridian light source 12. The dichroic mirror 14 serving as a mirror unit is an optical element which reflects only the light having a specific wavelength and transmits the light having other wavelengths, and the excitation light is separated from a fluorescent light by the dichroic mirror 14.

The dichroic mirror 14 is disposed to be inclined at, for example, about 45° with respect to an incident light. Therefore, the excitation light incident from the lens 13 is reflected by the dichroic mirror 14, namely, is bent at 90° to be directed in the downward direction.

The lens 13a is provided below the dichroic mirror 14. The lens 13c is provided below the lens 13a. The lens 13a and the lens 13c constitute a second lens. The polycrystalline diamond crystal 15 and a sample 50 to be a measuring target are disposed below the lens 13c.

The excitation light reflected by the dichroic mirror 14 is irradiated onto the diamond crystal 15 through the lens 13a and the lens 13c. In addition, the fluorescent light emitted from the diamond crystal 15 passes through the dichroic mirror 14.

The lens 13b serving as a third lens is provided above the dichroic mirror 14, and the image sensor 16 is provided above the lens 13b. The lens 13b collects the fluorescent light emitted from the diamond crystal 15 to irradiate the image sensor 16 with the fluorescent light. The image sensor 16 is, for example, a semiconductor sensor such as a CMOS image sensor (Complementary Metal Oxide Semiconductor Image Sensor), and receives a fluorescent image emitted from the diamond crystal 15.

The fluorescent image received by the image sensor 16 is output to the control unit 17 serving as a signal processing unit. The control unit 17 includes a signal processing circuit 18, a control circuit 19 and a microwave source 20. The signal processing circuit 18, the control circuit 19 and the microwave source 20 are formed in, for example, a semiconductor chip or the like.

The signal processing circuit 18 performs image processing on the input fluorescent image. The control circuit 19 is connected to the image sensor 16, the viridian light source 12 and the microwave source 20, and supplies a timing signal to the image sensor 16, the viridian light source 12 and the microwave source 20. In addition, the control circuit 19 performs control for setting a microwave frequency to the microwave source 20.

The coil 21 is connected to the microwave source 20 serving as a microwave unit. The coil 21 is configured to surround the peripheral portion of the diamond crystal 15 in a loop shape. The microwave source 20 supplies a microwave current to the coil 21.

With this configuration, a magnetic field of the microwave is generated around the diamond crystal 15. Note that the frequency of the microwave output from the microwave source 20 is set by the control circuit 19 as described above.

Here, in the magnetism measuring device 10, a ratio between the area of the image sensor 16 and the area of the diamond crystal 15 is set to be, for example, 1:n (n>1) by appropriately designing an optical system from the surface of the diamond crystal 15 to the image sensor 16.

The optical system which sets the area ratio between the image sensor 16 and the diamond crystal 15 to be 1:n includes the lens 13a, the lens 13c and the lens 13b. The lenses 13a and 13c magnify the excitation light reflected by the dichroic mirror 14 and irradiate the diamond crystal 15 with the excitation light.

In addition, the lenses 13a and 13c collect the fluorescent light emitted from the diamond crystal 15. The fluorescent light collected by the lenses 13a and 13c passes through the dichroic mirror 14 and is irradiated onto the image sensor 16 through the lens 13b.

In this manner, since the excitation light reflected by the dichroic mirror 14 is magnified by the lenses 13a and 13c to be irradiated onto the diamond crystal 15, the light source unit 11 positioned above the diamond crystal 15 can be made smaller than the diamond crystal 15.

Namely, the viridian light source 12, the lenses 13, 13a, 13b and 13c, the dichroic mirror 14, the image sensor 16 and the control unit 17 can be contained within the projection area of the diamond crystal 15.

In the case where the magnetism measuring device is used as a sensor of the biomagnetism measuring device, it is desirable that the diamond crystals are densely arranged without a gap in order to realize high spatial resolution as described in the section of SUMMARY OF THE INVENTION above.

However, in the configuration in which the image sensor or the like is larger than the projection area of the diamond crystal, it becomes difficult to densely arrange the diamond crystals without a gap because the arrangement is constrained by the size of the image sensor or the like when arranging the magnetism measuring devices.

On the other hand, in the case of the magnetism measuring device 10 illustrated in FIG. 1, the area of the diamond crystal 15 is the largest. Therefore, the light source unit 11, the image sensor 16 and the control unit 17 provided above the diamond crystal 15 can be contained within the projection area of the diamond crystal 15.

With this configuration, when arranging the magnetism measuring devices 10, the diamond crystals 15 can be densely arranged without a gap and without being hindered by the image sensor 16 or the like. Therefore, the high spatial resolution can be realized by using the magnetism measuring device 10 as a sensor of the biomagnetism measuring device.

Note that, in FIG. 1, the area ratio between the image sensor 16 and the diamond crystal 15 is set to be 1:n by using the two lenses 13a and 13c, but this can be realized also by one lens by the appropriate optical lens design.

In addition, the control unit 17 may be provided outside and connected through an external line or the like instead of disposing it within the projection area of the diamond crystal 15.

(Configuration Example of Diamond Crystal and Image Sensor)

Figure 2:
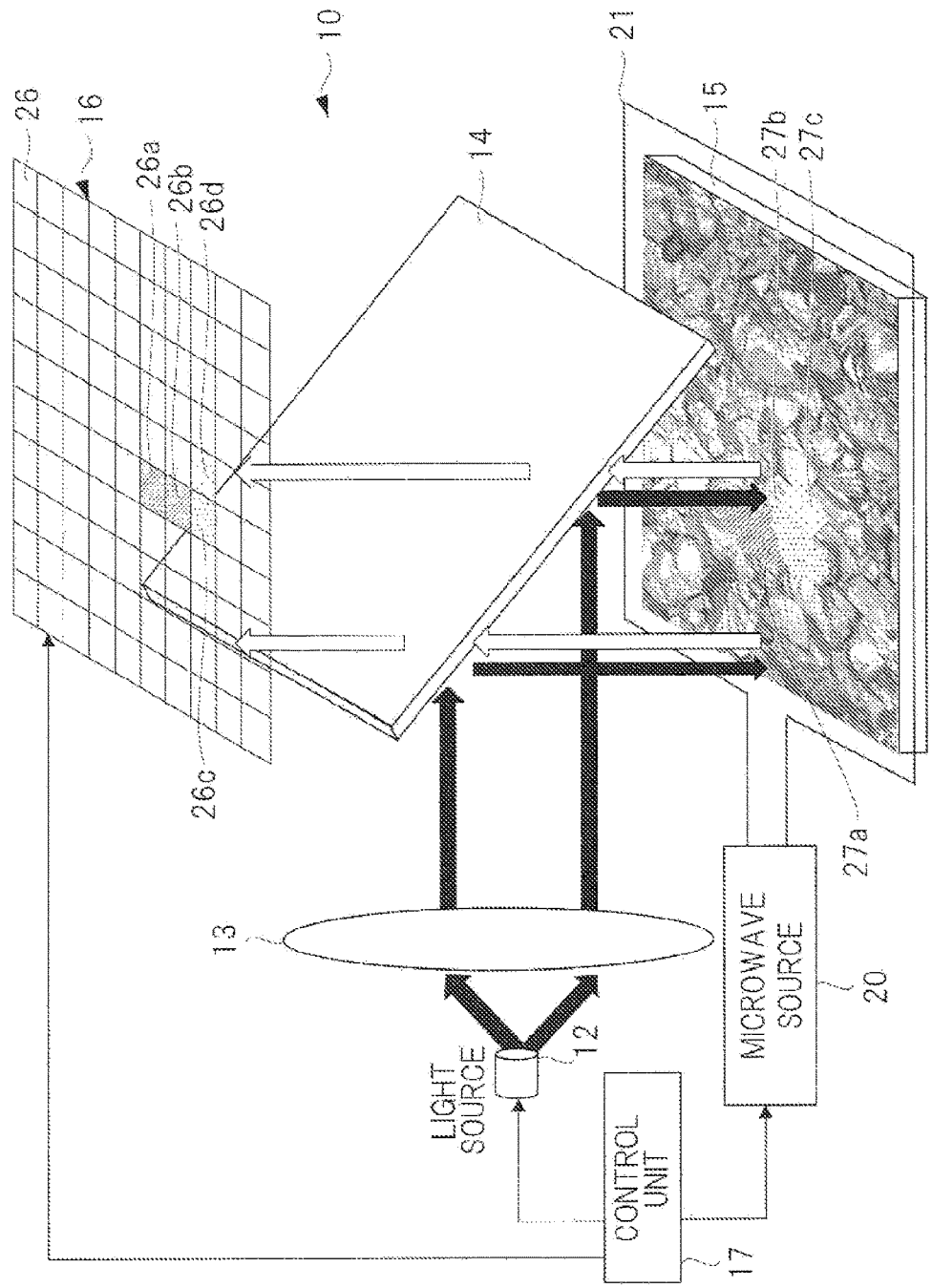
FIG. 2 is an explanatory diagram illustrating an example of a correspondence between crystalline regions of a diamond crystal and pixels of an image sensor in the magnetism measuring device of FIG. 1.

FIG. 2 is an explanatory diagram illustrating an example of a correspondence between crystalline regions of the diamond crystal 15 and pixels 26a to 26d of the image sensor 16 in the magnetism measuring device 10 of FIG. 1. Note that the illustration of the lenses 13a to 13c is omitted from FIG. 2 for the sake of simplicity.

The image sensor 16 has a configuration in which pixels 26 serving as light receiving elements are regularly arranged in a matrix shape. In addition, the diamond crystal 15 is made of polycrystalline as described above. In the current technology, the polycrystalline diamond crystal 15 having a diameter of, for example, about 30 mm has been reported.

On the other hand, in the case of a monocrystalline diamond crystal, the diamond crystal having an area of several square millimeters is available.

Therefore, in the magnetism measuring device 10, it is important to make it possible to use the polycrystalline diamond crystal in order to widen the area of the diamond crystal.

When the polycrystalline diamond crystal is used, it is desirable that the crystalline region of the diamond crystal 15 which is projected to a single pixel of the image sensor 16 is a single region. This is because a crystal orientation of a fluorescent output generating source detected by the pixel can be specified to a single orientation.

Here, the fluorescent light source incident on each of the pixels 26 can be made to be one crystalline region by setting the ratio between the pixels 26 of the image sensor 16 and the crystalline regions of the diamond crystal 15 to be 1:n.

Then, by performing calibration after assembling the magnetism measuring device 10, the orientation of the crystalline region corresponding to each pixel 26 of the image sensor 16 can be specified and stored in the image sensor 16. Since the processing of a signal output from the image sensor 16 can be performed for each pixel 26, it is possible to perform the correction of the crystal orientation of each crystalline region in the signal processing.

FIG. 2 illustrates a case where the crystalline region projected to the single pixel 26 is a single region and a case where a plurality of crystalline regions are projected to one pixel 26. The example in which the projected crystalline region is a single region is depicted by the pixels 26a and 26b and a crystalline region 27a represented by hatching in FIG. 2. The example in which the plurality of crystalline regions are projected is depicted by the pixels 26c and 26d and crystalline regions 27b and 27c represented by dots in FIG. 2.

Figure 3:
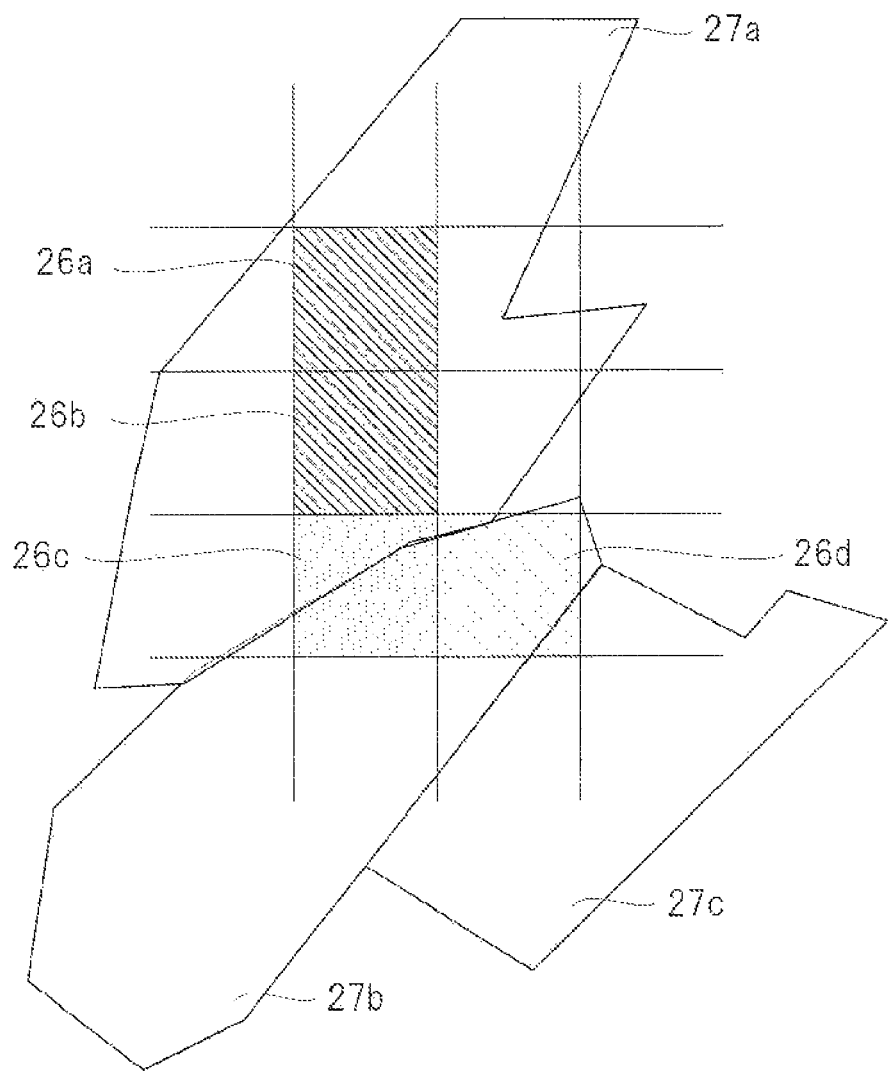
FIG. 3 is an enlarged explanatory diagram illustrating the correspondence between the crystalline regions of the diamond crystal and the pixels of the image sensor in the magnetism measuring device of FIG. 2.

FIG. 3 illustrates a detailed positional relation between the crystalline regions 27a, 27b and 27c and the pixels 26a, 26b, 26c and 26d to which these regions are projected. The crystalline region 27a and the crystalline region 27b are projected to the pixel 26c, and the crystalline regions 27a, 27b and 27c are projected to the pixel 26d, and thus these are not the pixels which receive the fluorescent light from a single crystalline region.

In the case where the crystalline region projected to the single pixel 26 is a single region, an ODMR (Optically Detected Magnetic Resonance) spectrum indicating a dependency of the fluorescent output on the microwave frequency is acquired for each of the external magnetic fields by applying the known external magnetic fields of at least three orientations to the diamond crystal 15 before the magnetic field is measured, whereby the crystal orientation of the crystalline region projected to each pixel 26 can be specified to a single orientation.

In addition, in the case where the plurality of crystalline regions are projected to one pixel 26, the pixel is eliminated from the magnetic field measurement, or if a dominant single orientation can be specified, the orientation may be used as an approximate orientation representing the pixel.

Figure 4:
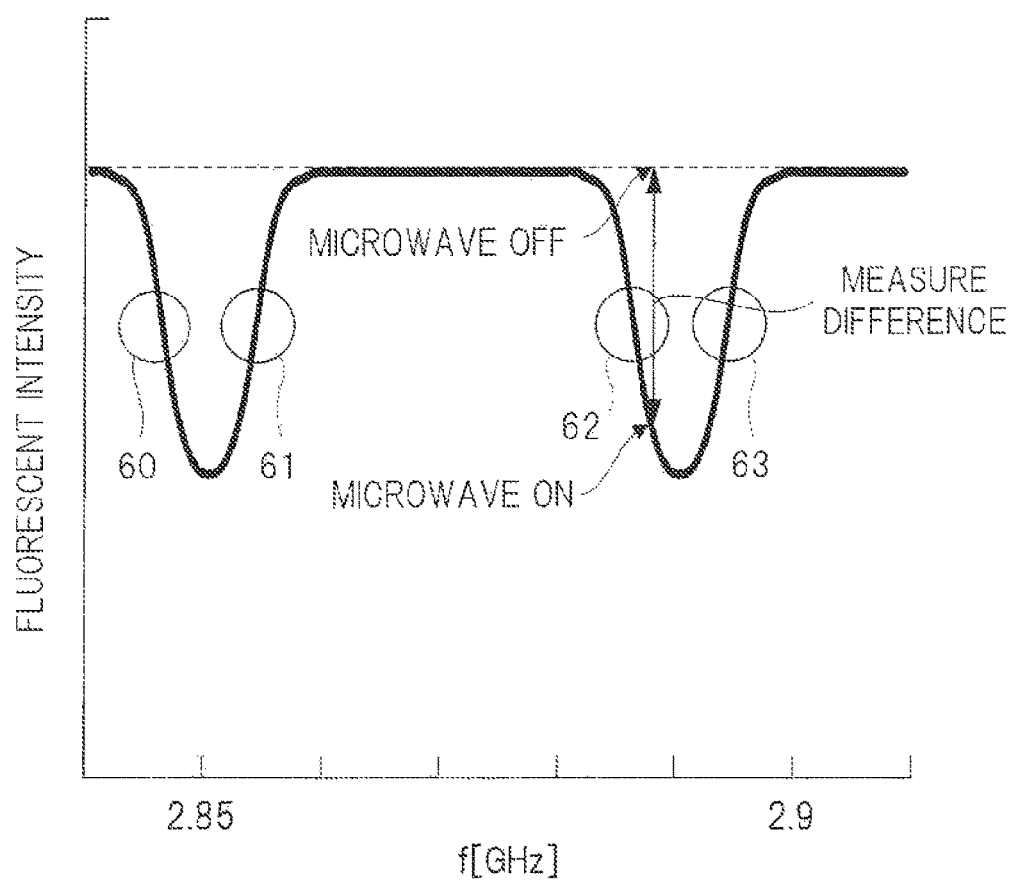
FIG. 4 is an explanatory diagram illustrating an example of a waveform near a fluorescence intensity decreased point in a microwave frequency spectrum of a fluorescence intensity.

FIG. 4 illustrates an example of the ODMR spectrum. In this drawing, the horizontal axis indicates a frequency of the microwave output from the microwave source 20, and the vertical axis indicates a fluorescence intensity of the diamond crystal 15.

For the accurate estimation of the crystal orientation from the ODMR spectrum, it is advantageous to use the steepest slopes 60 to 63 of the "valleys" of the waveform. A "valley" position on the low frequency side is estimated as an intermediate value of the slope 60 on the low frequency side and the slope 61 on the high frequency side of the "valley" on the low frequency side.

Similarly, a "valley" position on the high frequency side is estimated as an intermediate value of the slope 62 on the low frequency side and the slope 63 on the high frequency side of the "valley" on the high frequency side. A magnetic field sensed by nitrogen-vacancy pairs is obtained as a difference between the "valley" position on the high frequency side and the "valley" position on the low frequency side, and as a ratio between the magnetic field and a known applied magnetic field, a cosine value of an angle formed by a nitrogen-vacancy axis and a direction of the applied magnetic field can be determined. By performing the measurement like this to the applied magnetic fields of three orientations, the crystal orientation can be specified to a single orientation.

In the described-above manner, when arranging the magnetism measuring devices 10, the diamond crystals 15 can be densely arranged without a gap. As a result, the spatial resolution can be improved by using the magnetism measuring device 10 for the biomagnetism measuring device and others, and the high-sensitivity biomagnetism measuring device can be realized.

(Second Embodiment)

<Outline>

In the second embodiment, an example in which the ratio between the area of the image sensor 16 and the area of the diamond crystal 15 is set to be 1:n while simplifying the configuration compared to the magnetism measuring device 10 in FIG. 1 of the first embodiment will be described.

(Configuration Example of Magnetism Measuring Device)

Figure 5:
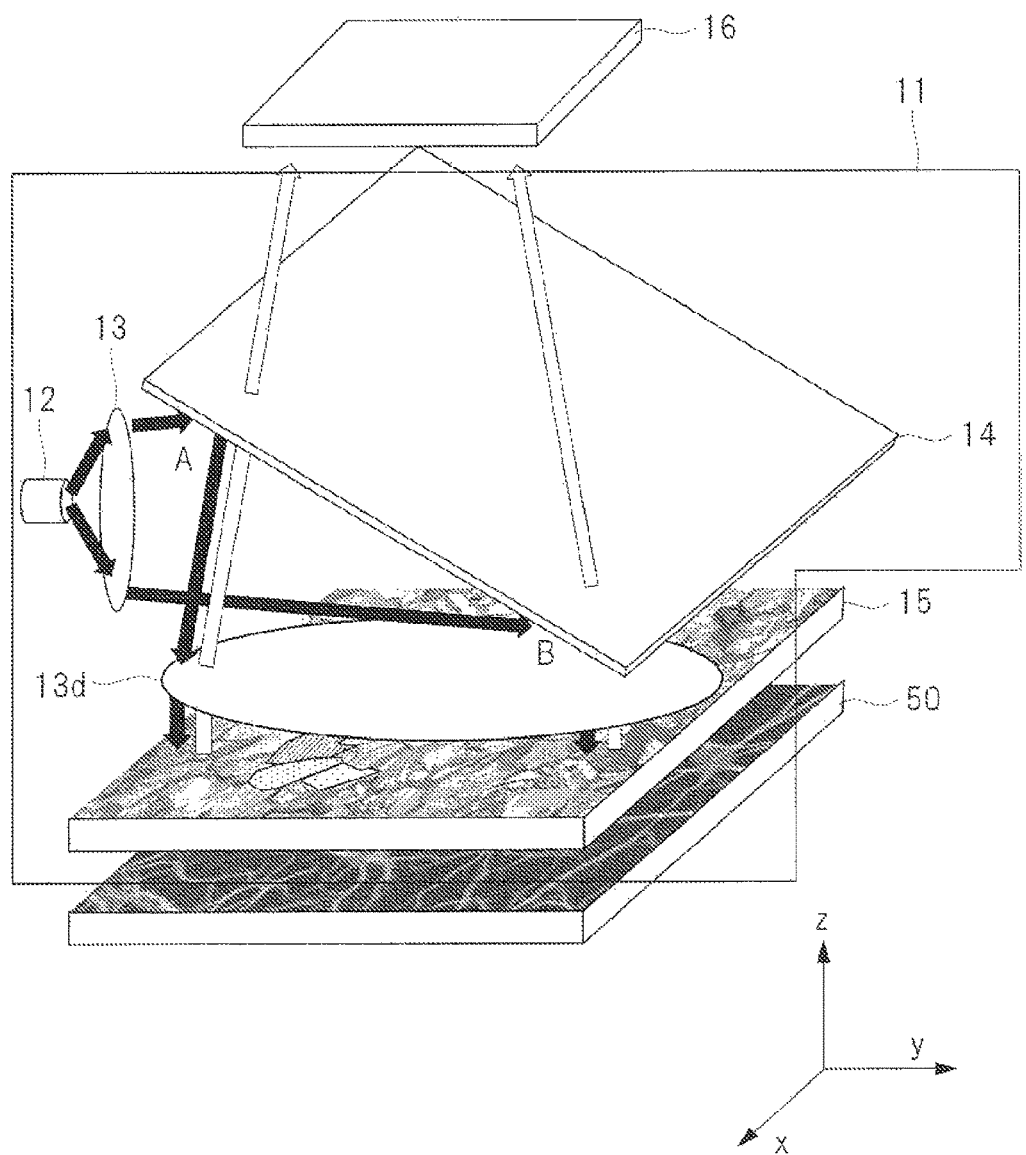
FIG. 5 is an explanatory diagram illustrating an example of a configuration of a magnetism measuring device according to the second embodiment.

FIG. 5 is an explanatory diagram illustrating an example of a configuration of the magnetism measuring device 10 according to the second embodiment.

Like the case of FIG. 1 of the first embodiment, the magnetism measuring device 10 of FIG. 5 includes a light source unit 11, the diamond crystal 15, the image sensor 16, a control unit 17 and a coil 21. Note that the illustration of the control unit 17 and the coil 21 is omitted in FIG. 5 for the sake of simplicity.

The magnetism measuring device 10 of FIG. 5 is different from the magnetism measuring device 10 of FIG. 1 in the configuration of the light source unit 11. Namely, the configuration having four lenses of the lenses 13, 13a, 13b and 13c is illustrated in FIG. 1, while the magnetism measuring device 10 of FIG. 5 is configured to have two lenses of the lens 13 and a new lens 13d.

The lens 13d magnifies the excitation light reflected by the dichroic mirror 14 to irradiate the diamond crystal 15 with the excitation light, and collects the fluorescent light emitted from the diamond crystal 15 to irradiate the image sensor 16 with the fluorescent light.

In addition, in the magnetism measuring device 10 of FIG. 1, the dichroic mirror 14 is disposed so as to form an incident angle of, for example, about 45° with respect to the incident light. Meanwhile, in the magnetism measuring device 10 of FIG. 5, the dichroic mirror 14 is disposed so as to form an incident angle larger than about 45° with respect to the incident light. In other words, the dichroic mirror 14 is disposed so as to form a shallower angle with respect to the diamond crystal 15. The other configurations are the same as those of FIG. 1 of the first embodiment, and thus the description thereof will be omitted.

For example, the dichroic mirror 14 has a structure in which a dielectric thin film is stacked on a glass surface. Here, when a refractive index of the dielectric thin film is n, a thickness thereof is t, a wavelength of the excitation light is λ, and an incident angle of the excitation light with respect to the dichroic mirror 14 is α, the total reflection occurs on the following condition.

$t = \lambda/2/n/\tan \alpha$

Since the excitation light is a monochromatic light, λ is constant.

Here, for the sake of explanation, the xyz coordinates are designated for the positional relation between the image sensor 16 and the polycrystalline diamond crystal 15.

The image sensor 16 and the diamond crystal 15 each are positioned in the xy plane. The z axis is a direction perpendicular to each of the image sensor 16 and the diamond crystal 15. Since the incident angle α is different at a point A and a point B illustrated in FIG. 5, the thickness t of the dielectric thin film on the dichroic mirror 14 is linearly inclined in the z direction. Therefore, even when the incident angle with respect to the dichroic mirror 14 is different at the point A and the point B, the excitation light can be totally reflected toward the diamond crystal 15.

In the wavelength bandwidth and the incident angle of the fluorescent output, the fluorescent output can be input to the image sensor 16 by preventing the above-mentioned total reflection condition from being satisfied. This includes a case where the dichroic mirror 14 has an area equal to that of the crystalline surface of the diamond crystal 15.

In the above-described manner, the number of lenses to be used can be reduced, and the surface of the dichroic mirror 14 can be disposed to be closer in parallel to the diamond crystal 15. Therefore, a distance in the height direction of the magnetism measuring device 10 can be reduced, namely, the thickness of the magnetism measuring device 10 can be reduced.

Accordingly, it is possible to achieve further size reduction of the magnetism measuring device 10 in addition to the effect of the first embodiment. Furthermore, since the number of components of the magnetism measuring device 10 can be reduced, it is possible to achieve the weight reduction.

(Third Embodiment)

<Outline>

In the third embodiment, a technology for achieving the further thickness reduction of the magnetism measuring device 10 by adopting the configuration of a mirrorless module will be described.

(Configuration Example of Magnetism Measuring Device)

Figure 6:
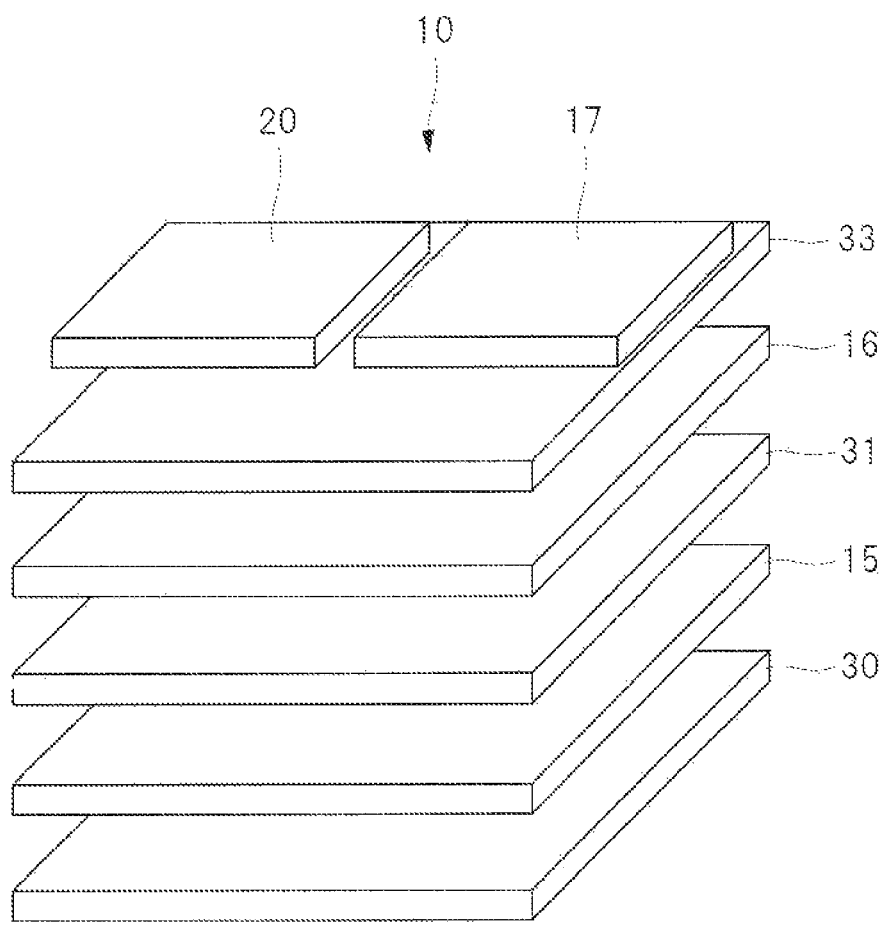
FIG. 6 is a schematic diagram illustrating an example of a configuration of a magnetism measuring device according to the third embodiment.

FIG. 6 is a schematic diagram illustrating an example of a configuration of the magnetism measuring device 10 according to the third embodiment.

FIG. 6 illustrates the magnetism measuring device 10 having the configuration of a mirrorless module.

As illustrated in FIG. 6, the magnetism measuring device 10 has a configuration made up of a radio frequency chip 30, a diamond crystal 15, a light source array 31, an image sensor 16, a package substrate 33, a control unit 17 and a microwave source 20.

The diamond crystal 15 is stacked above the radio frequency chip 30, and the light source array 31 serving as a light source chip is provided above the diamond crystal 15. The image sensor 16 is stacked above the light source array 31, and the package substrate 33 is stacked above the image sensor 16. In addition, the microwave source 20 and the control unit 17 each are mounted above the package substrate 33.

(Detailed Configuration Example of Magnetism Measuring Device)

Subsequently, a detailed configuration of the magnetism measuring device 10 will be described with reference to FIG. 7.

Figure 7:
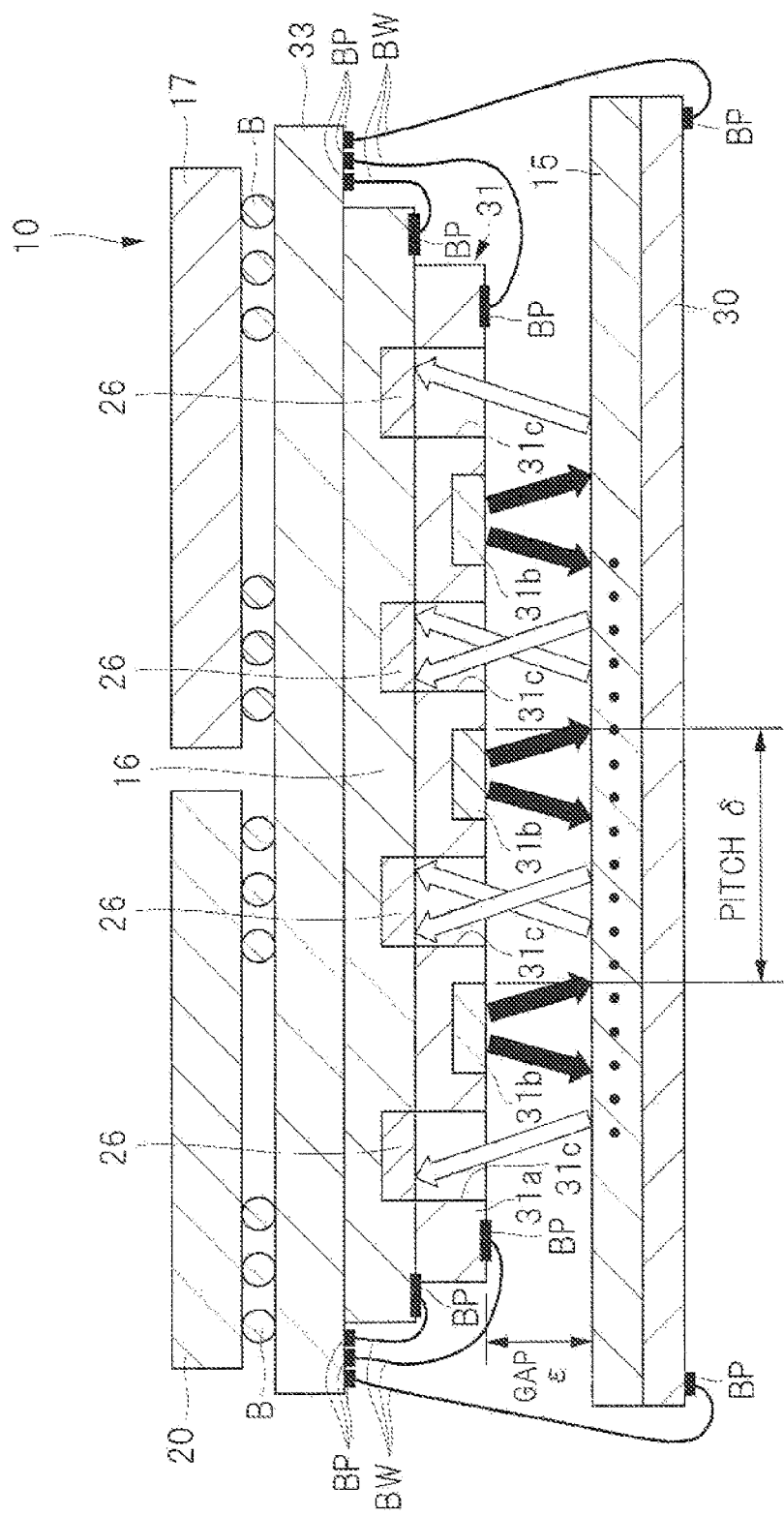
FIG. 7 is an explanatory diagram illustrating an example of a detailed configuration of the magnetism measuring device of FIG. 6.

FIG. 7 is an explanatory diagram illustrating an example of a detailed configuration in the magnetism measuring device 10 of FIG. 6.

The package substrate 33 is made of, for example, a multilayer printed substrate. The microwave source 20 and the control unit 17 each constituted of semiconductor chips are mounted on the main surface of the package substrate 33 via bumps B such as solder balls.

Here, the control unit 17 is made up of the signal processing circuit 18 and the control circuit 19 illustrated in FIG. 1 of the first embodiment. Further, in FIG. 6, the control unit 17 made up of the signal processing circuit 18 and the control circuit 19 and the microwave source 20 are formed in separate chips, but these may be formed in one chip.

The image sensor 16 is mounted on the rear surface of the package substrate 33, and the light source array 31 is mounted below the image sensor 16. The diamond crystal 15 is provided below the light source array 31 via an insulating film (not illustrated) formed of silicon dioxide ($SiO_2$) or the like. The radio frequency chip 30 is mounted below the diamond crystal 15.

Bonding pads BP are respectively formed in two facing side parts or four side parts of the package substrate 33, the image sensor 16, the light source array 31 and the radio frequency chip 30.

The bonding pad BP of the package substrate 33 and the bonding pad BP of the image sensor 16 are connected through a bonding wire BW. Similarly, the bonding pad BP of the package substrate 33 and the bonding pad BP of the light source array 31 are connected through the bonding wire BW, and the bonding pad BP of the package substrate 33 and the bonding pad BP of the radio frequency chip 30 are connected through the bonding wire BW, respectively.

In addition, the microwave source 20 and the radio frequency chip 30 are electrically connected through the bonding pad BP of the radio frequency chip 30, the bonding wire BW, the bonding pad BP of the package substrate 33, a wiring pattern (not illustrated) formed in the package substrate 33 and the bump B.

The light source array 31 and the control unit 17 are electrically connected through the bonding pad BP of the light source array 31, the bonding wire BW, the bonding pad BP of the package substrate 33, the wiring pattern of the package substrate 33 and the bump B.

Similarly, the image sensor 16 and the control unit 17 are electrically connected through the bonding pad BP of the image sensor 16, the bonding wire BW, the bonding pad BP of the package substrate 33, the wiring pattern of the package substrate 33 and the bump B.

The radio frequency chip 30 is made of, for example, a dielectric chip and an antenna (not illustrated) is formed in the surface of the dielectric chip. For example, the antenna is configured to surround the peripheral portion of the diamond crystal 15 in a loop shape.

Here, for example, the radio frequency chip 30 may be configured to include a plurality of radio frequency circuit units in which a frequency conversion circuit is paired with the antenna. In this case, each of the antennas is formed to correspond to each region of the diamond crystal 15, and each of the radio frequency circuit units emits microwaves of different frequencies to each region of the diamond crystal 15.

The diamond crystal 15 is mounted on the main surface of the radio frequency chip 30. The radio frequency chip 30 applies a microwave current supplied from the microwave source 20 to the antenna, thereby irradiating the diamond crystal 15 with the microwave.

The light source array 31 is provided above the diamond crystal 15 with a predetermined gap interposed therebetween. In the light source array 31, light emitting units 31$b$ are formed in an array shape on the main surface of a substrate 31$a$ such as a semiconductor substrate. The light emitting unit 31$b$ is made of, for example, a light emitting diode or a semiconductor laser diode. The control of a light-emitting operation in the light emitting unit 31$b$ is performed by the control circuit 19 of the control unit 17.

In addition, in the substrate 31$a$ of the light source array 31, a through light path 31$c$ is formed between the respective light emitting units 31$b$. The light emitting unit 31$b$ outputs the excitation light. The through light path 31$c$ is a hole through which the fluorescent light emitted from the diamond crystal 15 passes.

The main surface of the image sensor 16, that is, the surface on which the pixels are formed is bonded to an upper part of the light source array 31, that is, the rear surface of the light source array 31. The image sensor 16 is mounted on the main surface of the package substrate 33. The fluorescent light emitted from the diamond crystal 15 passes through the through light path 31$c$ of the light source array 31, and is irradiated onto each of the pixels 26 of the image sensor 16.

In addition, as described above, the microwave source 20 and the control unit 17 made of the semiconductor chips are respectively mounted on the rear surface of the package substrate 33.

Then, the radio frequency chip 30, the diamond crystal 15, the light source array 31, the image sensor 16, the package substrate 33, the control unit 17 and the microwave source 20 are sealed by, for example, a thermosetting resin, so that a rectangular package (not illustrated) is formed.

(Example of Connection Relation of Magnetism Measuring Device)

Figure 8:
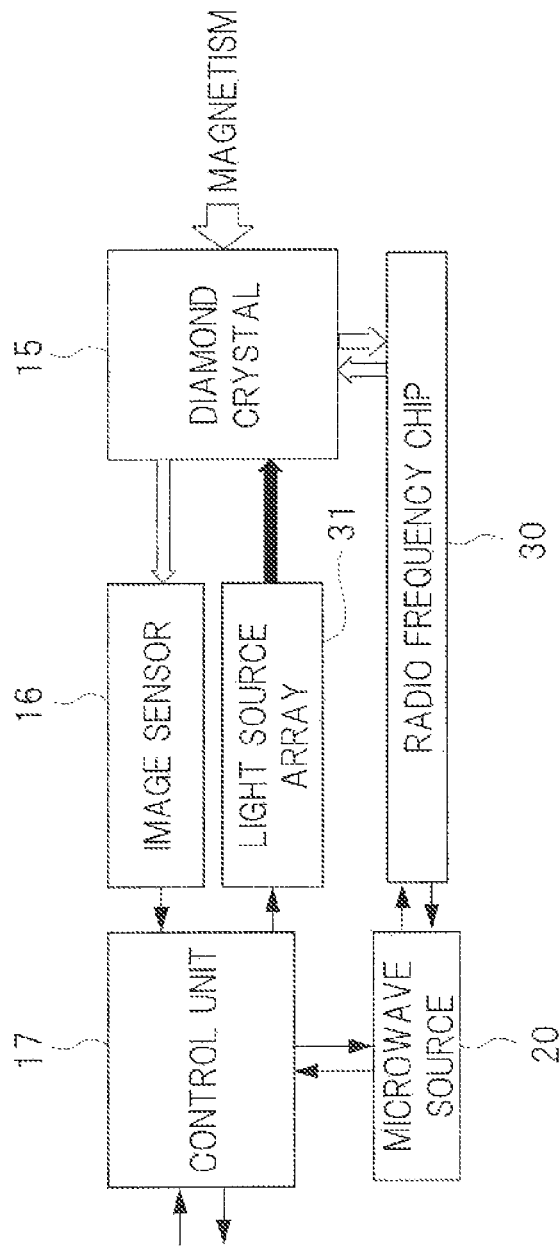
FIG. 8 is an explanatory diagram illustrating a connection relation of the respective blocks in FIG. 7.

FIG. 8 is an explanatory diagram illustrating a connection relation of the respective blocks in the magnetism measuring device 10 of FIG. 7.

As illustrated in the drawing, the microwave having a frequency of, for example, about 2.87 GHz is applied to the diamond crystal 15 by the radio frequency chip 30. The control unit 17 controls the microwave source 20. The microwave source 20 sets a microwave frequency based on the control of the control unit 17.

The light emitting unit 31b of the light source array 31 irradiates the diamond crystal 15 with the excitation light. The fluorescent light emitted from the diamond crystal 15 passes through the through light path 31c and is irradiated onto the image sensor 16. Then, the fluorescent image received by the image sensor 16 is subjected to the image processing by the signal processing circuit 18 of the control unit 17.

Here, as illustrated in FIG. 7, a pitch of the light emitting units 31b in the light source array 31 is set to a pitch δ. In this case, the pitch of the light emitting units 31b is a minimum inter-light-source distance between the light emitting unit 31b and the light emitting unit 31b. In addition, a gap between the light source array 31 and the diamond crystal 15 is defined as a gap ε. The gap ε is set to approximately the pitch δ between the light emitting units 31b. Here, the pitch δ is defined as a first distance, and the gap ε is defined as a second distance.

In this manner, by setting the gap ε to approximately the pitch δ, the excitation light output from the light emitting unit 31b of the light source array 31 is irradiated onto the entire surface of the diamond crystal 15, and the fluorescent output from the diamond crystal 15 can be efficiently detected by the image sensor 16.

As a result, the radio frequency chip 30 positioned below the diamond crystal 15 and the light source array 31, the image sensor 16, the package substrate 33, the control unit 17 and the microwave source 20 positioned above the diamond crystal 15 can be disposed so as to be contained within the projection area of the diamond crystal 15.

In this manner, it is possible to fabricate a module configuration in which the radio frequency chip 30, the diamond crystal 15, the light source array 31, the image sensor 16, the package substrate 33, the control unit 17 and the microwave source 20 are stacked.

With the module configuration like this, the lens and the dichroic mirror are no longer necessary. Therefore, it is possible to achieve the size reduction of the magnetism measuring device 10, in particular, the size reduction in a thickness direction in addition to the effect of the first embodiment.

(Example of Wearable Diagnosis Device)

Figure 9:
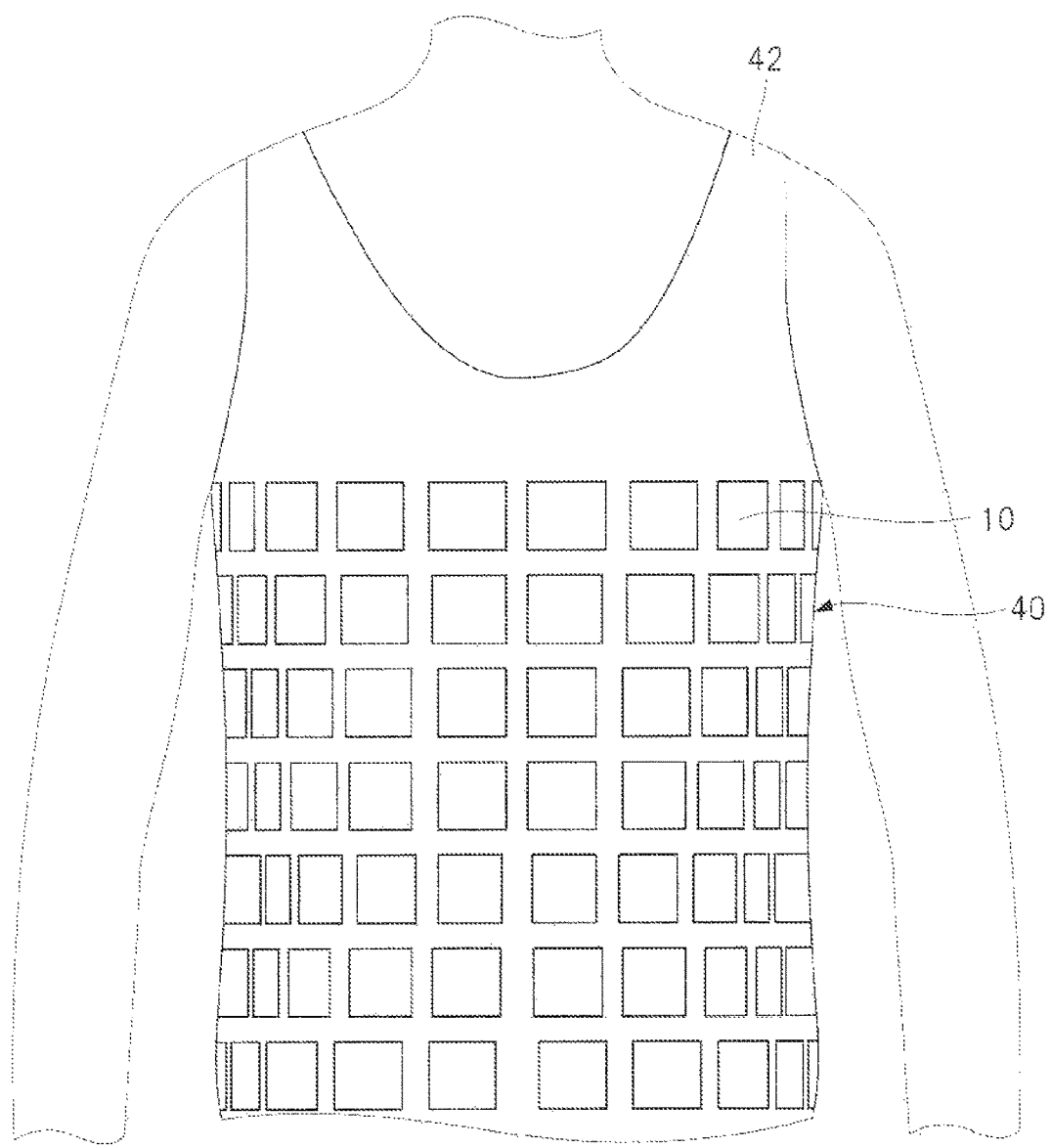
FIG. 9 is an explanatory diagram illustrating an example of a wearable diagnosis device using the magnetism measuring device of FIG. 7.

The magnetism measuring device reduced in thickness is effectively applied particularly to a wearable diagnosis device. FIG. 9 is an explanatory diagram illustrating an example of a wearable diagnosis device 40 using the magnetism measuring device 10 of FIG. 7.

As illustrated in the drawing, the wearable diagnosis device 40 is constituted of, for example, the magnetism measuring devices 10 attached to a garment 42 such as a shirt. In this manner, the magnetism measuring devices 10 are arranged on the human body surface to detect the information of the inner body.

In the wearable diagnosis device 40, a detectable depth depends on a sensitivity of the magnetism measuring device 10 serving as a sensor, and the spatial resolution depends on a surface density of the magnetism measuring devices 10. As the surface density increases, high spatial resolution can be realized up to a deep position.

Since the magnetism measuring devices 10 having the module configuration as illustrated in FIG. 7 can be densely arranged on the body surface without a gap, it is possible to realize the wearable diagnosis device capable of detecting the information of the deep body with high resolution.

In addition, since the magnetism measuring device 10 is reduced in size, the wearable diagnosis device 40 having a less oppressive feeling and a light weight can be realized, so that it is possible to reduce a burden of a patient who puts on the wearable diagnosis device 40.

Note that, although an example of the wearable diagnosis device 40 using the magnetism measuring device 10 of FIG. 7 has been described here, the wearable diagnosis device 40 may be configured by attaching, for example, the magnetism measuring device 10 described in the first and second embodiments (FIGS. 1 and 5).

(Another Configuration Example of Magnetism Measuring Device)

Figure 10:
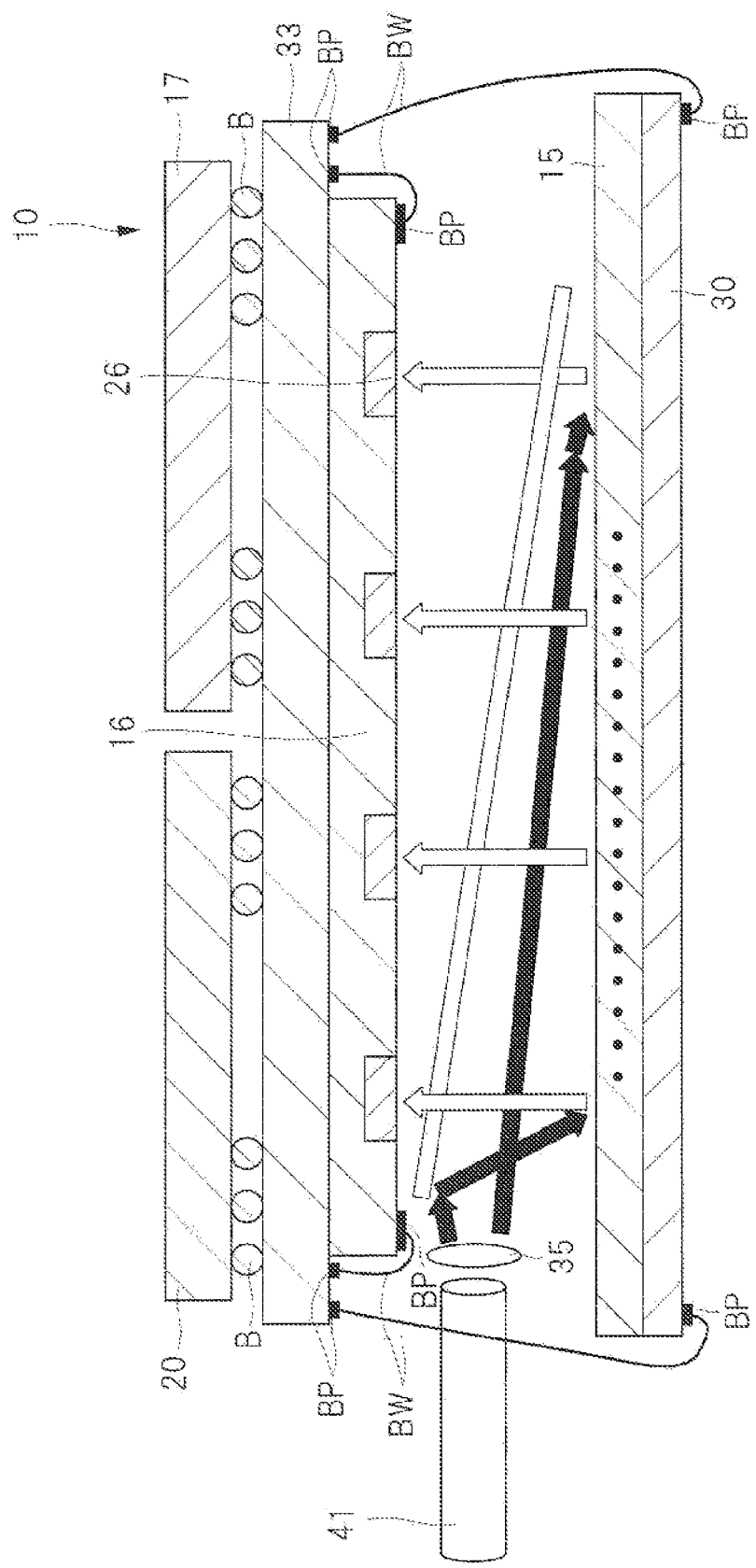
FIG. 10 is an explanatory diagram illustrating another example of a configuration of the magnetism measuring device of FIG. 7.

FIG. 10 is an explanatory diagram illustrating another configuration example of the magnetism measuring device 10 of FIG. 7.

The magnetism measuring device 10 of FIG. 10 is different from the magnetism measuring device 10 of FIG. 7 in that the light source array 31 is removed and a lens 35 is newly added.

The lens 35 serving as a fourth lens is provided near a peripheral portion on one side of the diamond crystal 15 and the image sensor 16. The lens 35 is irradiated with the excitation light from an optical fiber 41 serving as the light source unit inserted into a side surface of the package (not illustrated) of the magnetism measuring device 10.

The optical fiber 41 is a light transmission path and is formed of a center core made of a fine fibrous material such as quartz glass or plastic and a cladding which covers the core. The core has a refractive index higher than that of the cladding, and the light is propagated in a state of being confined in the core by a phenomenon called a total reflection.

The excitation light emitted from the optical fiber 41 is magnified by the lens 35, and then irradiated onto the diamond crystal 15. Then, the fluorescent light emitted from the diamond crystal 15 is received by the image sensor 16. Note that the other configurations are the same as those of FIG. 8, and thus the description thereof will be omitted. With this configuration, since the light source array 31 is no longer necessary, the magnetism measuring device 10 can be further reduced in thickness.

(Another Example of Wearable Diagnosis Device)

Figure 11:
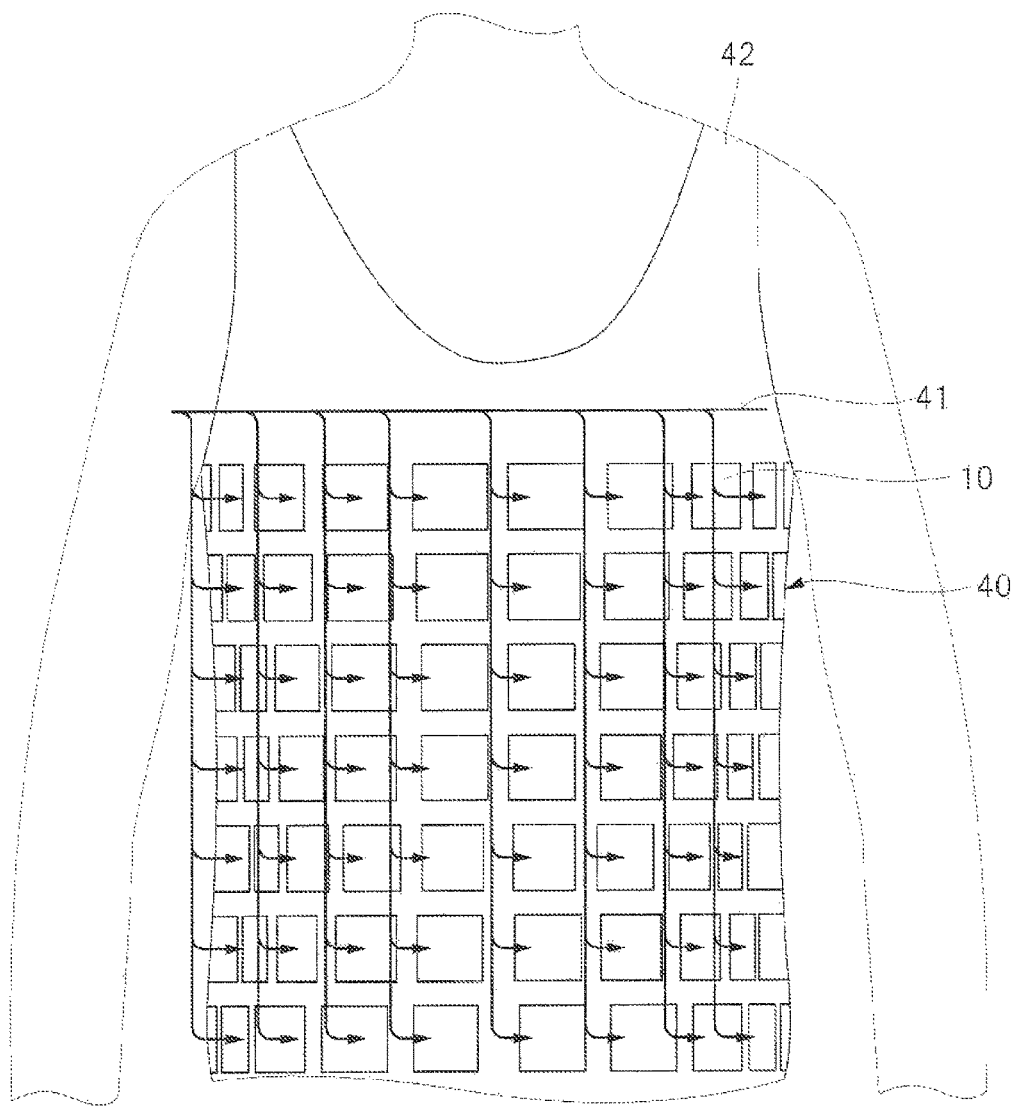
FIG. 11 is an explanatory diagram illustrating an example of a wearable diagnosis device using the magnetism measuring device of FIG. 10.

FIG. 11 is an explanatory diagram illustrating an example of a wearable diagnosis device 40 using the magnetism measuring device 10 of FIG. 10.

Also in the wearable diagnosis device 40 of FIG. 11, the magnetism measuring devices 10 are attached to, for example, a garment 42 such as a shirt like the case of FIG. 9, and the magnetism measuring devices 10 are densely arranged on the body surface without a gap. In addition, the optical fibers 41 are also attached to the garment 42, and the excitation light is emitted from the end portions of the respective optical fibers 41 to the lens 35.

By using the magnetism measuring device 10 reduced in size as described above, it is possible to reduce a burden of the patient who puts on the wearable diagnosis device 40.

(Timing Example of AC Magnetic Field Measurement of MRI Magnetic Resonance Imaging Measurement)

Figure 12:
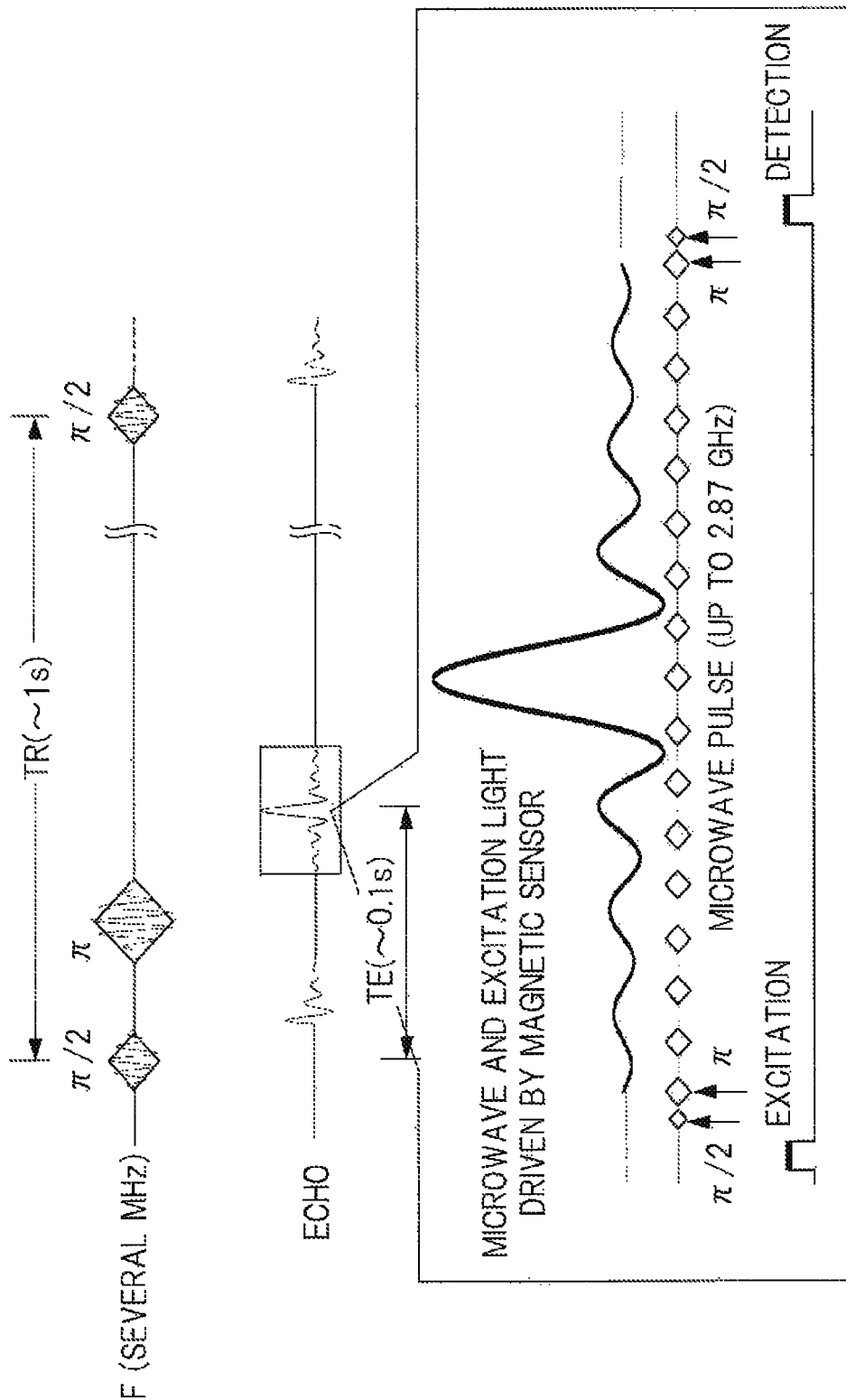
FIG. 12 is an explanatory diagram illustrating an example of timing of an AC magnetic field measurement in an MRI measurement using the wearable diagnosis device illustrated in FIG. 9 and others.

FIG. 12 is an explanatory diagram illustrating an example of timing of the AC magnetic field measurement in the MRI measurement using the wearable diagnosis device 40 illustrated in FIG. 9 and others.

As illustrated in FIG. 12, after a π/2 pulse and a π pulse of the microwave are added at a time interval of TE/2, an echo, that is, a measuring target occurring after the elapse of TE/2 is measured.

The π pulse is a microwave pulse (about 2.87 GHz) having an intensity and a time length corresponding to the energy that inverts the spin of the nitrogen-vacancy pairs by π (180°, and the π/2 pulse is a pulse having the energy corresponding to the half of the π pulse.

In order to measure the amplitude of the AC magnetic field to be measured, first, the diamond crystal 15 is irradiated with the excitation light before the arrival of the echo.

Thereafter, the π/2 pulses and the π pulse columns (plural) of the microwave are applied. The π/2 and π pulses are applied at timing when the AC signal of the echo traverses the zero. After the last π/2 pulse, an echo signal intensity is measured as the fluorescence intensity of the diamond crystal 15.

In the case where the wearable diagnosis device 40 illustrated in FIG. 9 and others is put on, an MRI signal can be measured even when an inclined magnetic field is suppressed within a range generable by a wound coil. Thus, it is possible to reduce the entire size of the MRI apparatus.

(First Configuration Example of MRI Apparatus)

Figure 13:
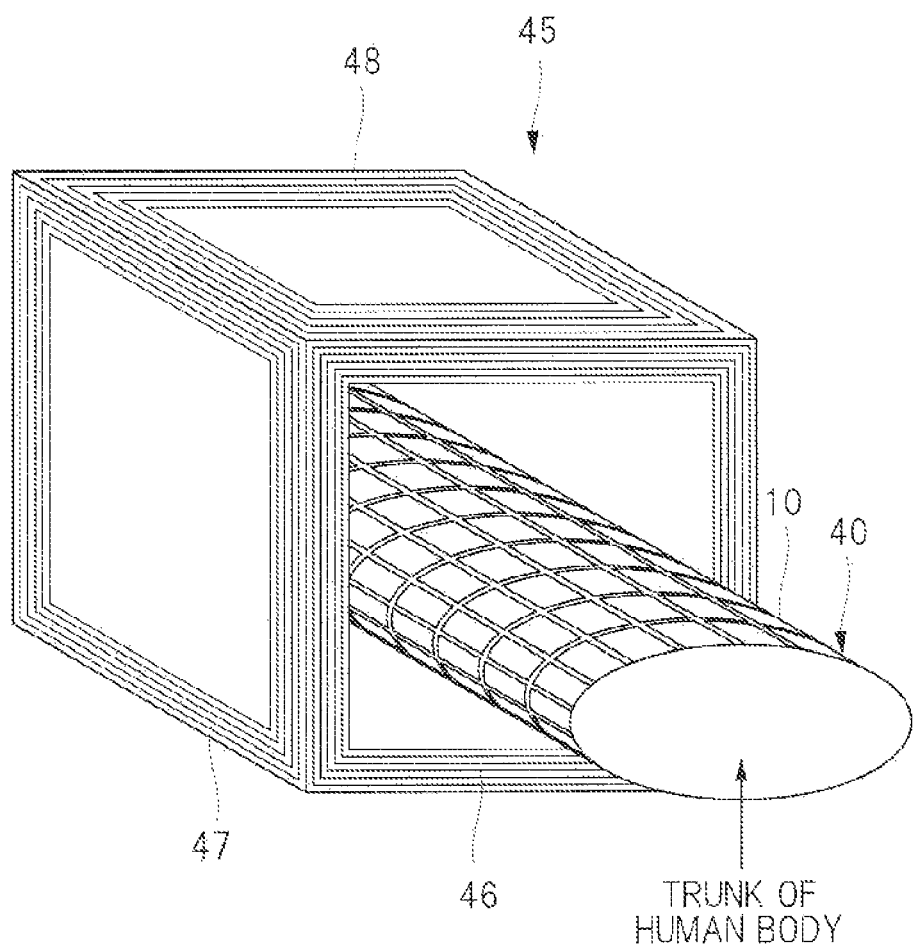
FIG. 13 is an explanatory diagram illustrating an example of a configuration of an MRI apparatus using the wearable diagnosis device illustrated in FIG. 9 and others.

FIG. 13 is an explanatory diagram illustrating an example of a configuration in an MRI apparatus 45 using the wearable diagnosis device 40 illustrated in FIG. 9 and others.

In the MRI apparatus 45 illustrated in FIG. 13, magnetic field generation coils 46 to 48 are arranged on the outside of the measuring target in three axial directions of the X direction, the Y direction and the Z direction. The inclined magnetic field can be applied to the measuring target by applying an appropriate DC current to these magnetic field generation coils 46 to 48.

By applying an RF (radio frequency) pulse in a state where the inclined magnetic field is applied, protons of the cross section selected in accordance with a relation between the intensity of the inclined magnetic field and the RF frequency can be excited. The echo signal generated by the excited protons is measured by the respective magnetism measuring devices 10.

In the above-described manner, the MRI signal in the cross section can be acquired.

(Second Configuration Example of MRI Apparatus)

Figure 14:
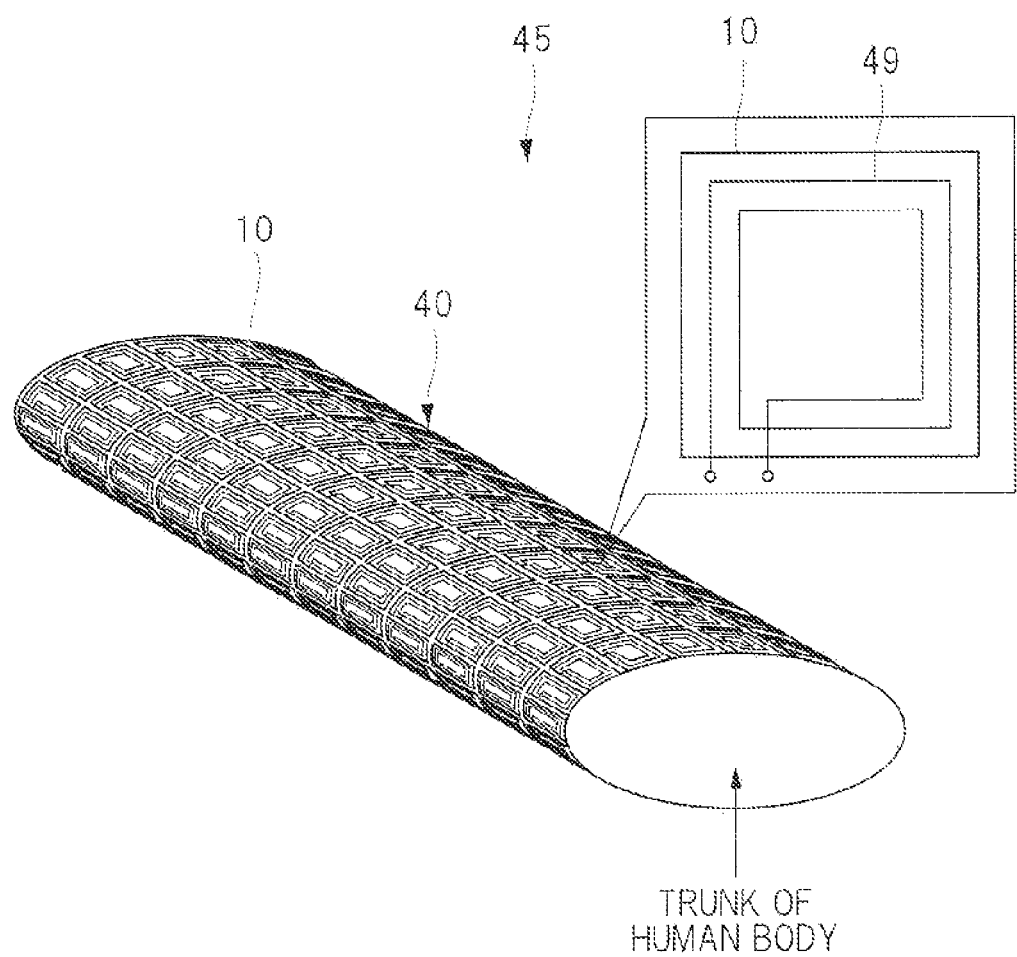
FIG. 14 is an explanatory diagram illustrating another example of a configuration of the MRI apparatus using the wearable diagnosis device illustrated in FIG. 9 and others.

In addition, FIG. 14 is an explanatory diagram illustrating another example of the configuration in the MRI apparatus 45 using the wearable diagnosis device 40 illustrated in FIG. 9 and others.

In the MRI apparatus 45 of FIG. 14, an inclined magnetic field generation coil 49 is integrally formed with the respective magnetism measuring devices 10. With this configuration, the magnetic field generation coils 46 to 48 illustrated in FIG. 13 are no longer necessary, and it is possible to achieve the further size reduction of the MRI apparatus 45.

In the foregoing, the invention made by the inventors of the present invention has been concretely described based on the embodiments. However, the present invention is not limited to the foregoing embodiments and various modifications and alterations can be made within the scope of the present invention.

Note that the present invention is not limited to the embodiments described above and includes various modification examples. For example, the embodiments above have been described in detail so as to make the present invention easily understood, and the present invention is not limited to the embodiment having all of the described constituent elements.

Also, a part of the configuration of one embodiment may be replaced with the configuration of another embodiment, and the configuration of one embodiment may be added to the configuration of another embodiment. Furthermore, another configuration may be added to a part of the configuration of each embodiment, and a part of the configuration of each embodiment may be eliminated or replaced with another configuration.

What is claimed is:

1. A magnetism measuring device comprising:
a diamond crystal having a plurality of nitrogen-vacancy pairs;
an image sensor configured to detect an intensity of a fluorescent light emitted from the diamond crystal by a plurality of pixels; and
a light source unit configured to irradiate the diamond crystal with an excitation light and irradiate the image sensor with the fluorescent light emitted from the diamond crystal,
wherein the image sensor and the light source unit are disposed above the diamond crystal in a direction perpendicular to a main surface of the diamond crystal so that projected areas of the image sensor and the light source unit fall within an area of the main surface of the diamond crystal, and
wherein, viewed in the direction perpendicular to the main surface of the diamond crystal, the diamond crystal overlaps an entirety of the sensor.

2. The magnetism measuring device according to claim 1, further comprising:
a microwave unit configured to irradiate the diamond crystal with a microwave;
a signal processing unit configured to process a fluorescent image received by the image sensor; and
a control unit configured to control operations of the light source unit, the microwave unit and the signal processing unit,
wherein the microwave unit, the signal processing unit and the control unit are disposed so as to be contained within a projection area of the diamond crystal.

3. The magnetism measuring device according to claim 2, wherein the light source unit includes:
a light source configured to output an excitation light;
a first lens configured to collect the excitation light output from the light source;
a mirror unit configured to separate the excitation light and the fluorescent light;
a second lens configured to magnify the excitation light separated by the mirror unit to irradiate the diamond crystal with the magnified excitation light, and collect the fluorescent light emitted from the diamond crystal; and a third lens configured to collect the fluorescent light separated by the mirror unit to irradiate the image sensor with the collected fluorescent light.

4. The magnetism measuring device according to claim 3, wherein a magnification of the second lens is set so as to make an area ratio between the image sensor and the diamond crystal be 1:n, and n is more than one.

5. The magnetism measuring device according to claim 1, wherein the light source unit is made up of a light source chip which irradiates the diamond crystal with an excitation light, and
wherein the light source chip includes: a plurality of light emitting units which are formed in an array shape and emit an excitation light; and
a through light path which is formed in the array shape between the respective light emitting units and transmits the fluorescent light emitted from the diamond crystal.

6. The magnetism measuring device according to claim 5, wherein a first distance corresponding to a gap between adjacent light emitting units is equal to a second distance corresponding to a gap between the light source chip and the diamond crystal.

7. The magnetism measuring device according to claim 5, further comprising:
a microwave unit configured to irradiate the diamond crystal with a microwave;
a signal processing unit configured to process a fluorescent image received by the image sensor; and
a control unit configured to control operations of the light source unit, the microwave unit and the signal processing unit,
wherein the microwave unit, the signal processing unit and the control unit are disposed so as to be contained within a projection area of the diamond crystal.

8. The magnetism measuring device according to claim 1, wherein the light source unit includes a fourth lens configured to magnify an excitation light emitted from outside to irradiate the diamond crystal with the excitation light, and
wherein the fourth lens is disposed so as to be contained within a projection area of the diamond crystal.

9. The magnetism measuring device according to claim 3, wherein the light source is arranged in a space between the mirror unit and the second lens.

10. The magnetism measuring device according to claim 1,
wherein the light source unit includes:
a light source configured to output an excitation light;
a first lens configured to collect the excitation light output from the light source; and
a mirror unit configured to separate the excitation light and the fluorescent light, the mirror unit being disposed so as to form an incident angle larger than 45° with respect to the excitation light collected by the first lens.

11. The magnetism measuring device according to claim 1, wherein a ratio between a size the pixels of the image sensor to a size of ones of crystalline regions of the diamond crystal is 1:n (n>1).

12. The magnetism measuring device according to claim 1,
wherein the main surface of the diamond crystal is arranged facing towards the image sensor,
wherein the image sensor comprises a face facing towards the main surface,
wherein a perimeter of the face is defined by a periphery of the image sensor, and
wherein the main surface is larger in surface area than the face.

13. The magnetism measuring device according to claim 1,
wherein the image sensor comprises a face,
wherein the face of the image sensor is arranged facing the main surface of the diamond crystal,
wherein the main surface of the diamond crystal is arranged facing the face of the image sensor,
wherein an area of the face of the image sensor is less than an area of the main surface of the diamond crystal,
wherein the main surface of the diamond crystal comprises a first length from a first side of the main surface to a second side of the main surface,
wherein the first side of the main surface is opposite to the second side of the main surface across the main surface,
wherein the first length is perpendicular to the direction perpendicular to a main surface of the diamond crystal,
wherein the face of the image sensor comprises a second length from a first side of the face to a second side of the face,
wherein the first side of the face is opposite to the second side of the face across the face,
wherein the first length is parallel to the second length, and
wherein the second length is less than half of the first length.

14. The magnetism measuring device according to claim 1, wherein the diamond crystal comprises a larger surface area than the image sensor and the light source unit together.

15. The magnetism measuring device according to claim 1,
wherein the image sensor and the light source unit are disposed above the diamond crystal in the direction perpendicular to the main surface of the diamond crystal, and
wherein a surface area of the image sensor and the light source unit combined falls within a projected surface area of the main surface of the diamond crystal.

16. A magnetism measuring device comprising:
a diamond crystal having a plurality of nitrogen-vacancy pairs;
an image sensor configured to detect an intensity of a fluorescent light emitted from the diamond crystal by a plurality of pixels; and
a light source unit configured to irradiate the diamond crystal with an excitation light and irradiate the image sensor with the fluorescent light emitted from the diamond crystal,
wherein the image sensor and the light source unit are disposed above the diamond crystal in a direction perpendicular to a main surface of the diamond crystal,
wherein a projected area of each of the image sensor and the light source unit is smaller than an area of the main surface of the diamond crystal when viewed from above of the image sensor, and
wherein, viewed in the direction perpendicular to the main surface of the diamond crystal, the diamond crystal overlaps an entirety of the image sensor.

* * * * *